United States Patent [19]
Anthony

[11] Patent Number: 5,970,210
[45] Date of Patent: Oct. 19, 1999

[54] HEATED RESPIRATORY THERAPY HUMIDIFIER

[75] Inventor: Jean-Michel Anthony, Steenhuffel, Belgium

[73] Assignee: Ponnet, Gilman & Anthony VOF, Kapellen, Belgium

[21] Appl. No.: 08/983,203
[22] PCT Filed: Aug. 29, 1996
[86] PCT No.: PCT/BE96/00090
  § 371 Date: Jan. 12, 1999
  § 102(e) Date: Jan. 12, 1998
[87] PCT Pub. No.: WO97/07845
  PCT Pub. Date: Mar. 6, 1997

[30] Foreign Application Priority Data

Aug. 28, 1995 [BE] Belgium .............................. 09500718

[51] Int. Cl.$^6$ .......................... A01G 13/06; C10K 15/00; B01D 47/00
[52] U.S. Cl. ........................... 392/386; 261/139; 261/104
[58] Field of Search ..................................... 392/386, 394, 392/395, 396, 403; 261/139, 140.2, 141, 142, 100, 102, 103, 104, 105–110, DIG. 65

[56] References Cited

U.S. PATENT DOCUMENTS

| | | | |
|---|---|---|---|
| 3,108,014 | 10/1963 | Gellar | 118/715 |
| 3,149,758 | 9/1964 | Bush et al. | 222/189.09 |
| 4,459,139 | 7/1984 | VonReis et al. | 96/6 |
| 4,571,244 | 2/1986 | Knighton | 210/446 |
| 4,657,713 | 4/1987 | Miller | 261/142 |
| 4,753,758 | 6/1988 | Miller | 261/139 |
| 4,943,704 | 7/1990 | Rabenau et al. | 219/275 |
| 5,109,471 | 4/1992 | Lang | 392/396 |
| 5,273,689 | 12/1993 | Hamasaki | 261/104 |
| 5,389,311 | 2/1995 | Hetzel | 261/104 |

FOREIGN PATENT DOCUMENTS

| | | | |
|---|---|---|---|
| 0 127 368 A2 | 12/1984 | European Pat. Off. | A61M 16/00 |
| 0 413 127 A | 7/1990 | European Pat. Off. | A61M 16/16 |
| 2 267 661 | 12/1993 | United Kingdom | A61M 167/10 |
| WO 92/07601 | 5/1992 | WIPO | A61M 16/00 |

*Primary Examiner*—Teresa Walberg
*Assistant Examiner*—Sam Paik
*Attorney, Agent, or Firm*—Fitch, Even, Tabin & Flannery

[57] ABSTRACT

An apparatus for compensating heat and humidity loss in a device that administers or restitutes air to a patient, amongst others in a device that comprises an air supply duct which extends between a respirator or an anaesthesia apparatus and the patient. The apparatus includes a housing with a coupling to be connected on this air supply duct, in which coupling a heating resistance is mounted, in which housing water is admitted. Further included in the housing is a membrane with water impermeable but water vapor permeable characteristics and an element that assures the desired heat level, in the coupling and air supply duct.

9 Claims, 4 Drawing Sheets

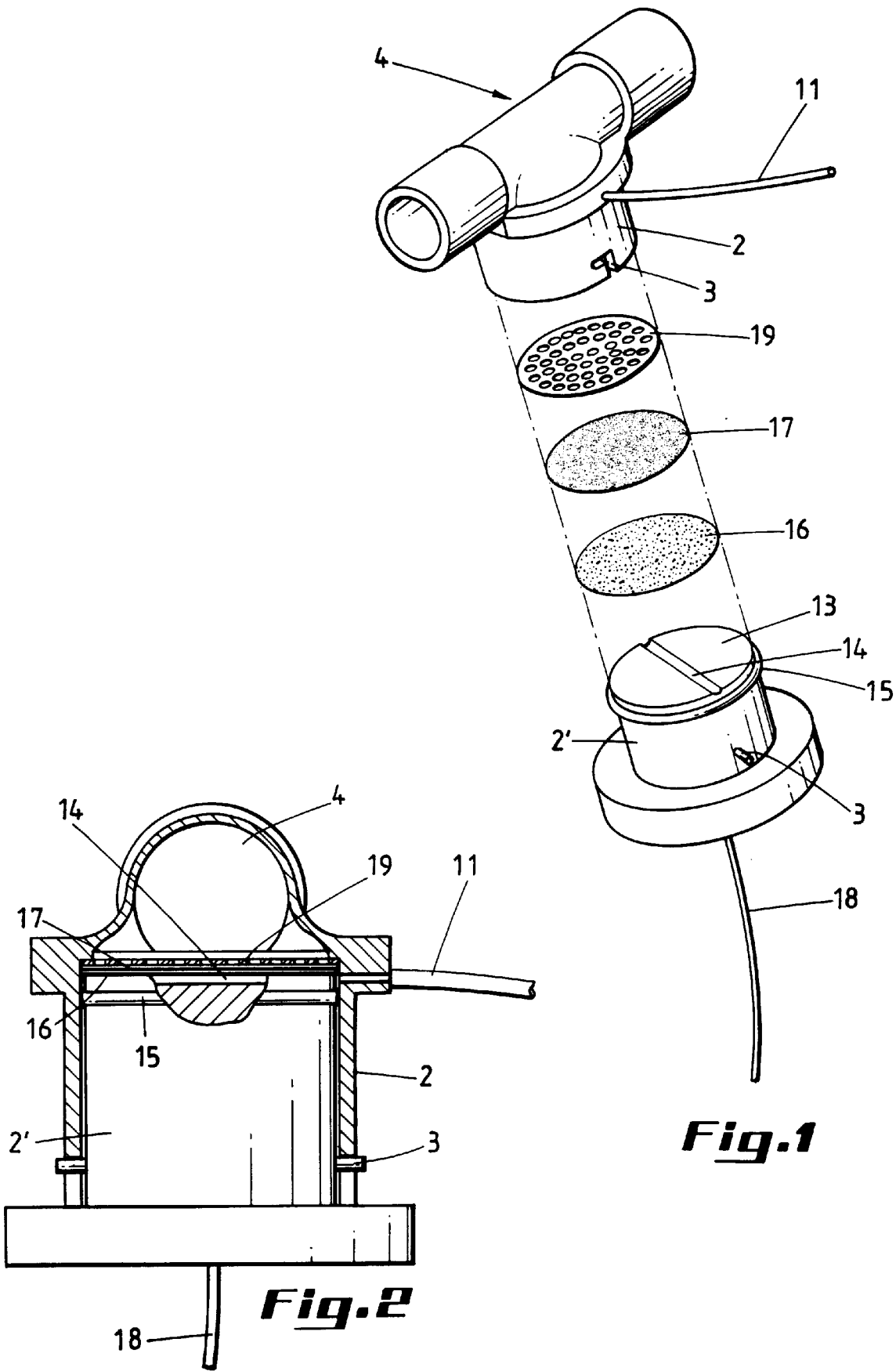

HEATED RESPIRATORY THERAPY HUMIDIFIER

This invention relates to an apparatus for compensating heat and humidity loss in a device that administers or restitutes warn and humid air to a patient, amongst others in a device that comprises an air supply duct which extends between a respirator or an anaesthesia apparatus and the patient.

The apparatus can thus as well be part of an artificial nose as be placed outside this artificial nose. Artificial noses are also known under the abbreviation H.M.E.

An object of the invention is to prescribe an apparatus that maintains the heat level and the humidity proportion of the circulating air at the requested level, can be connected in an air supply duct at an arbitrary localisation so that a very great flexibility of the device is assured.

A further very clear object of the invention is to propose a solution to the bothersome and sometimes dangerous occurrence for the patient, of too much condensation water in the air supply ducts appertaining to such an apparatus, so that the provision of water traps provided in all existing apparatuses until now are no longer needed.

To make this possible according to the invention, the apparatus according to the invention is characterised in that it has a connecting housing (1) with a coupling connected to this air supply duct, in which coupling a heating resistance is mounted, in which housing water is admitted, and further characterised by the presence in this housing of a membrane with water impermeable but water vapour permeable characteristics and of an element that assures the desired heat level in above mentioned coupling and air supply duct.

In a preferred embodiment the above mentioned element is a metal perforated plate acting like a heat exchanger.

According to a possible variant the above mentioned element is an additional heating resistance.

Still according to the invention the above mentioned housing is cylindrical and the above mentioned heating resistance is mounted in a cylindrical component, whereof the flat side, i.e. the side that is directed towards above mentioned membranes, comprises at least a transversal canal for the dispersion of the water admitted in the housing.

Other details and advantages of the invention will appear from the following description of an apparatus for compensating heat and humidity loss in a device that administers or restitutes warm and humid air to a patient.

The description is only given by way of example and does not limit the invention. The reference numbers relate to the hereto annexed figures.

FIG. 1 is a perspective exploded view representation of the apparatus according to the invention.

FIG. 2 is, at a greater scale, a longitudinal cross section through the apparatus according to the invention.

Figure 5:
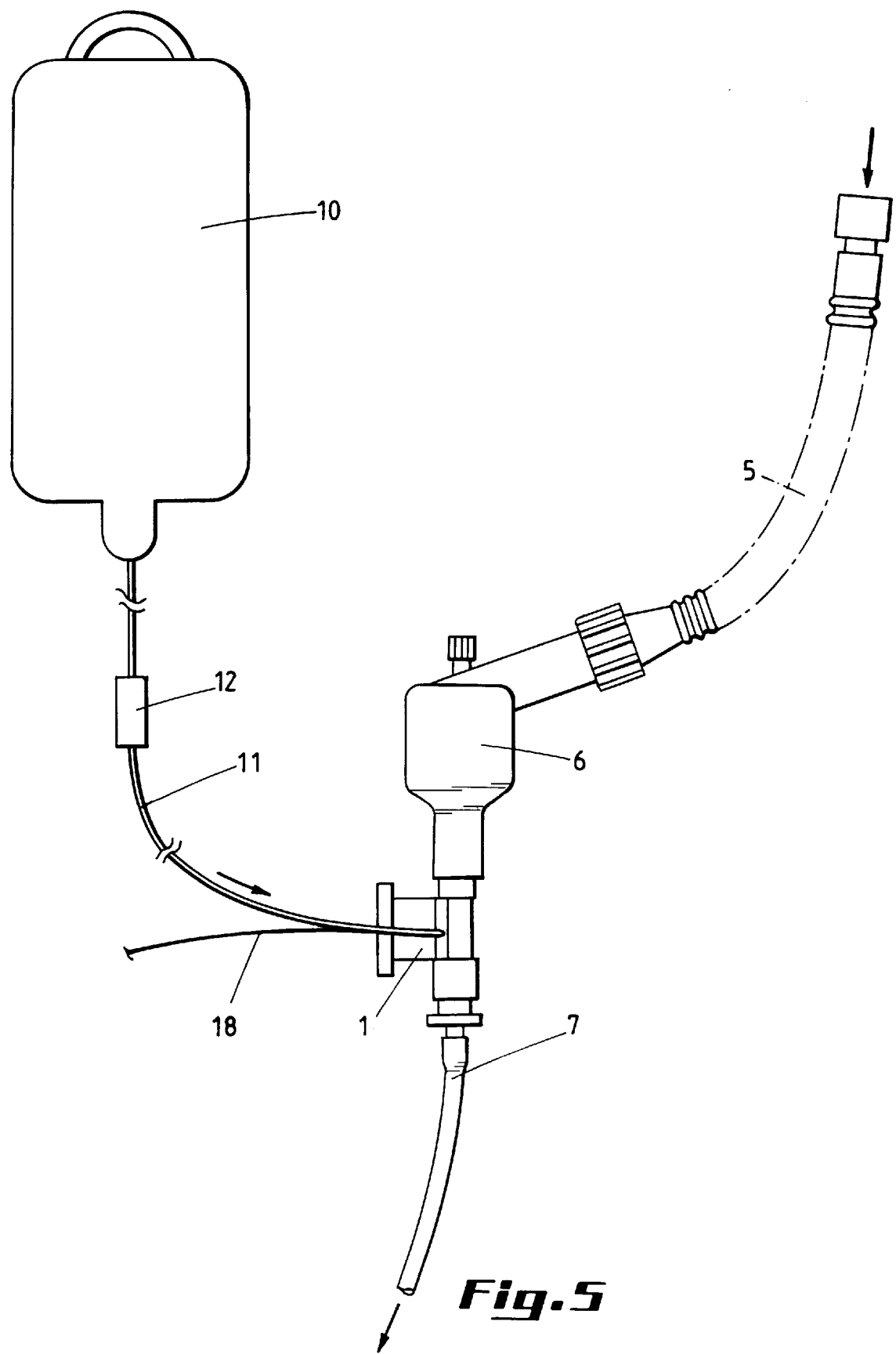

FIG. 5 schematically shows a device for the maintenance of an anaesthesia wherein the apparatus according to the invention is connected.

Figure 6:
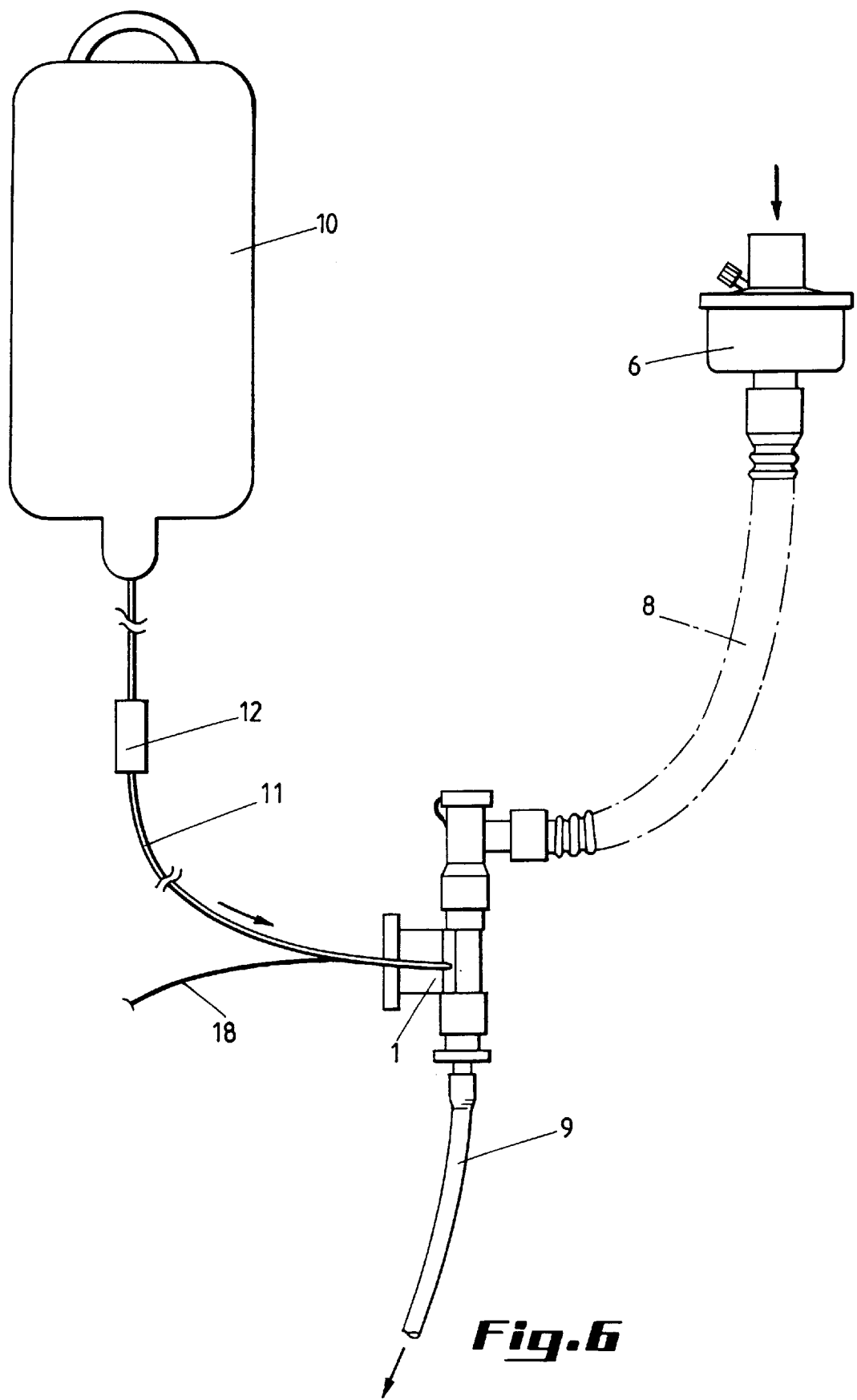

FIG. 6 schematically shows a respiratory device wherein the apparatus according to the invention is connected.

The apparatus represented by these figures and more particularly by FIG. 1, is composed of a housing 1 that is cylindrical in the most favourable embodiment.

The cylindrical housing is realised by fitting the cylindrical component 2 in the cylindrical component 2' with the smallest diameter. The fitting together of the cylindrical components 2 and 2' is realised by using an obvious solution, for example by using a bayonet catch 3.

On the cylindrical part 2 a coupling 4 is connected that, in use, is part of an air supply duct to a patient. The coupling described here is represented in form of a T, but it could take another form if needed. By air supply duct must be understood the part of the duct that is connected to a non illustrated anaesthesia or a non illustrated respiratory apparatus.

In FIG. 5 the duct 5 is represented which connects an anaesthesia apparatus with an artificial nose 6. Downstream of this artificial nose the apparatus according to the invention appears. Beyond this apparatus, indicated with its housing 1, the tracheal catheter 7 leads to the patient. In FIG. 6 another arrangement is represented wherein the duct 8 is mounted between an artificial nose 6 and the apparatus according to the invention, represented by its housing 1. Downstream of the apparatus according to the invention runs the air supply duct 9 to the patient.

In both cases water is admitted from a holder ID through a water supply duct 11 to the apparatus. In this duct 11 a droplet counter 12 is connected.

In the cylindrical housing of the apparatus according to the invention a heating resistance not represented in the figures is mounted in the cylindrical component 2' with the smallest diameter. Such a resistance is a self-adjusting resistance of the PTC-type.

With the reference 18 the electrical conductors are each time represented that lead to this heating resistance.

On the flat side 13 of the cylindrical component 2' at least one transversal canal 14 is provided. An O-ring 15 is mounted in a circular excavation of the wall of the cylindrical component 2' with the smallest diameter.

To achieve the object described in the preamble of this application, namely the maintenance at the desired level of heat and humidity of the air that must be administered to a patient, a membrane 16 with hydrophilic characteristics rests on the flat side 13. Hereupon rest then a second membrane, namely a water impermeable but water vapour permeable membrane 17. Both membranes can appear as a composite material, so that both membranes form a whole. The water that must be admitted in the apparatus, reaches the interior of the cylindrical component 2 via a water supply duct 11.

Figure 3:
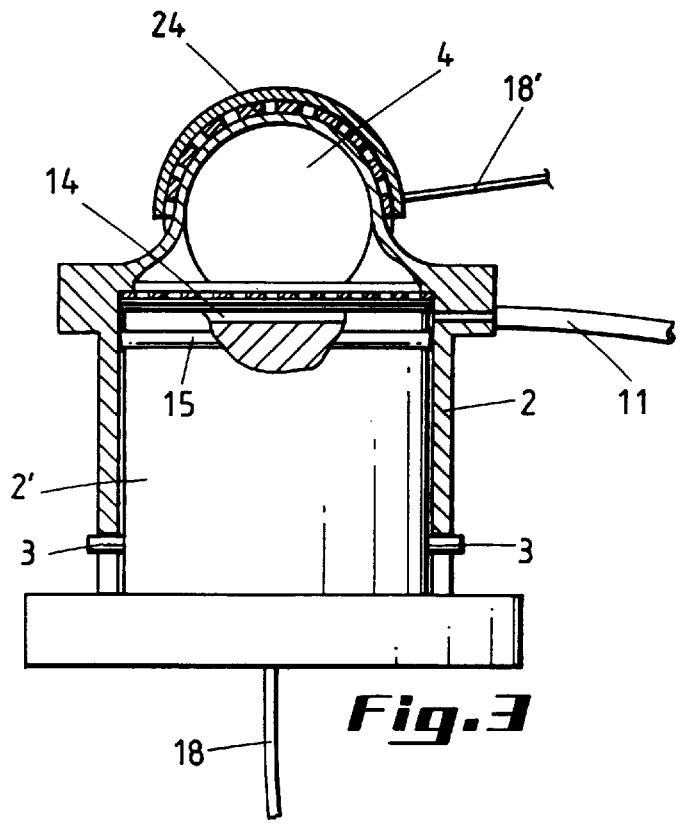
FIG. 3 is a longitudinal cross section, with a partial omission, for a first variant.
Figure 4:
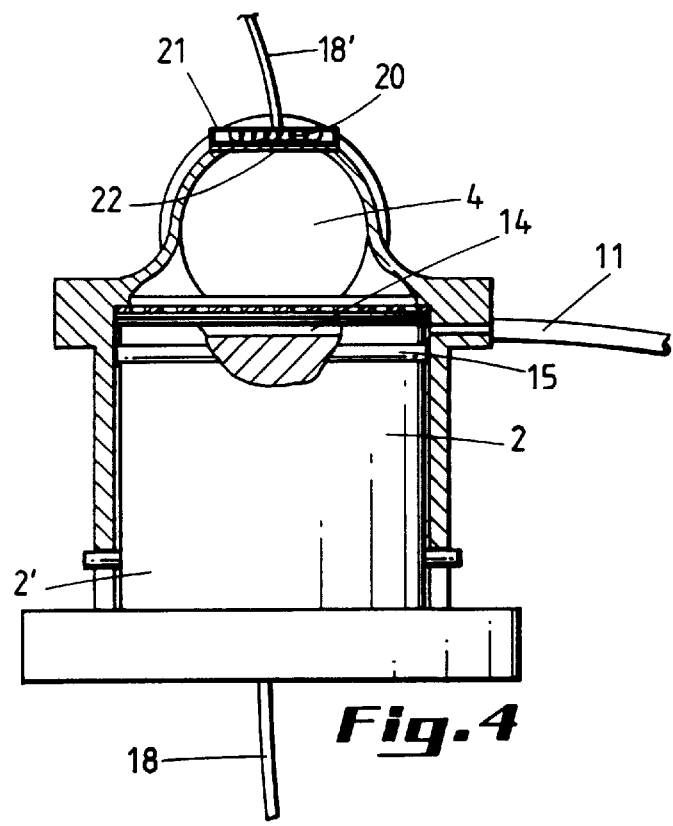
FIG. 4 is a longitudinal cross section, with a partial omission, for a second variant.

As can be derived from the sections according to FIGS. 2–4, the water flows in the apparatus just under the already earlier mentioned membranes 16 and 17 but above the flat side 13 of the cylindrical component 2' with the smallest diameter. In order to ensure an ideal diffusion of the water in the hydrophilic membrane 16, the flat side 13 of the cylindrical component 2' has at least a transversal canal 14. The water supplied through the water supply duct 11, is then diffused homogeneously over the flat side 13 and soaks the hydrophilic membrane 16 that rests on this flat side 13.

Since the membrane 17 shows water impermeable but water vapour permeable characteristics, the desired level of water vapour will be able to displace itself through this membrane.

Membranes with such characteristics are known and are used in different apparatuses with the same purpose. They can be made of porous P.T.F.E. glued to a support of micro glass fibres. Other membranes with the same characteristics can be used here.

Now in order to maintain by technically simple but yet reliable means the largest possible quantity of humid air brought at the desired temperature at a constant level and to supply it in this state to a patient, in the spirit of the invention, in the neighbourhood of the coupling 4, an element is connected that is composed of a perforated metal plate 19. FIG. 1 clearly shows such a perforated metal plate.

The same object could be achieved by replacing said metal plate 19 by an additional self-adjusting electric heating resistance.

In the variant according to FIG. 3 an additional heating resistance 24 is brought partially around a part of the coupling 4.

In the variant according to FIG. 4 the additional heating resistance 20 is mounted in a closed box 21. A plate 22 composed of light metal closes the opening that is provided for that purpose in the wall of the coupling 4.

In the three cases, namely. by using a perforated metal plate 19 (FIGS. 1 and 2), or by providing each time an additional heating resistance 24 (FIG. 3) or 20 (FIG. 4) the desired heat level is assured in the air supply ducts. Hereby is also prevented that condensation, extremely unfavourable for the patient, occurs in these ducts. With the reference 18' the electrical conductors are illustrated that assure the supply of the additional resistances 20, respectively 24.

To reduce condensation phenomena, the perforated metal plate 19 plays an essential role. The perforated metal plate 19 indeed works as a heat exchanger so that the circulating air is not only maintained at the desired ideal temperature by the water vapour liberated in the apparatus but also by this plate.

The heat exchange processed by the metal plate 19 is bi-directional and can thus influence by its <<feed-back>> characteristics the self-adjusting function of the heating resistance present in component 2', so that in case of a greater air flow this resistance will evaporate a greater quantity of water.

All heating resistances of the apparatus according to the invention are indeed of the P.T.C. type.

By strictly maintaining the temperature of the humid air in the apparatus under control, the formation of too much condensation water herein is prevented, which is an essential object of the invention.

The object of the invention is thus clearly the maintenance at the desired heat level of the water vapour in the ducts that administer or restitute air to a patient and to assure a humidity level whereby a minimum of condensation occurs in these ducts.

We shall finally note that the apparatus according to the invention can be used in paediatrics, be it without artificial nose.

I claim:

1. An apparatus for compensating heat and humidity loss in a device that administers or restitutes air to a patient, comprising an air supply duct which extends between a respirator or an anaesthesia apparatus and the patient, a T-shaped coupling in the air duct including an opening for communicating air with an interior of a housing containing a heating resistance, a membrane having water impermeable but water vapour permeable characteristics, apparatus for admitting water between the heating resistance and the membrane and a perforated metal plate in contact with a surface of the membrane and exposed to the opening for communication of water vapour and heat from the perforated plate.

2. An apparatus according to claim 1 wherein the above mentioned membrane is divided into a hydrophilic membrane and a water vapour permeable but water impermeable membrane.

3. An apparatus according to claim 1 comprising an additional heating resistance.

4. An apparatus according to claim 3, wherein the additional heating resistance is a resistance that is mounted in a closed box which is provided in an opening closed by a plate, provided in a wall of above mentioned T-shaped coupling connected in the air supply duct.

5. An apparatus according to claim 3, wherein the above mentioned additional resistance is a resistance that is partially fixed around the T-shaped coupling.

6. An apparatus according to claim 3 wherein the above mentioned housing is cylindrical and the heating resistance is mounted in a cylindrical component, whereof a flat side, is directed towards above mentioned membranes, and has at least a transverse canal for the diffusion of the water admitted in the housing.

7. An apparatus according to claim 6 wherein one of the membranes is a hydrophilic membrane that rests on the flat side of the cylindrical component.

8. An apparatus according to claim 7 wherein the membrane is of a material that is water impermeable but water vapour permeable, placed between the hydrophilic membrane and the metal plate.

9. An apparatus according to claim 1 wherein the housing is composed of two nestable cylindrical components with a sealing O-ring therebetween.

\* \* \* \* \*